United States Patent [19]
Tower

[11] Patent Number: 5,352,199
[45] Date of Patent: Oct. 4, 1994

[54] BALLOON CATHETER

[75] Inventor: Allen J. Tower, North Lawrence, N.Y.

[73] Assignee: Numed, Inc., Hopkinton, N.Y.

[21] Appl. No.: 68,928

[22] Filed: May 28, 1993

[51] Int. Cl.$^5$ .......................................... A61M 29/00
[52] U.S. Cl. ................................. 604/96; 606/194
[58] Field of Search ............................. 604/96–103; 606/192, 194

[56] References Cited

U.S. PATENT DOCUMENTS

| | | |
|---|---|---|
| 3,731,692 | 5/1973 | Goodyear . |
| 4,327,736 | 5/1982 | Inoue . |
| 4,346,698 | 8/1982 | Hanson et al. .................. 604/103 |
| 4,367,747 | 1/1983 | Witzel . |
| 4,439,186 | 3/1984 | Kuhl . |
| 4,490,421 | 12/1984 | Levy ................................. 604/96 |
| 4,555,242 | 11/1985 | Saudagar ......................... 604/96 |
| 4,652,258 | 3/1987 | Drach . |
| 4,748,982 | 5/1988 | Horzewaki . |
| 4,819,751 | 4/1989 | Shimada et al. ................ 606/194 |
| 4,820,349 | 4/1989 | Saab ................................ 606/194 |
| 4,986,830 | 1/1991 | Owens et al. .................... 604/95 |
| 5,019,042 | 5/1991 | Sahota .............................. 604/96 |

Primary Examiner—C. Fred Rosenbaum
Assistant Examiner—Frank Wilkens
Attorney, Agent, or Firm—Harris Beach & Wilcox

[57] ABSTRACT

There is disclosed a balloon catheter wherein the balloon is fabricated of a high pressure, ultra-thin wall modified polyethylene terephthalate copolymer, and has a desired memorized shape. In a preferred embodiment the balloon has a central waist-like configuration suitable for valvuloplasty. The polymer can be heat-shaped and retains or memorizes a desired shape thereafter. The balloon is blow-molded and attached to a catheter for inflation through a lumen thereof. When inflated to a first low pressure it assumes the desired shape, and rounds out after a second inflating pressure is achieved.

6 Claims, 2 Drawing Sheets

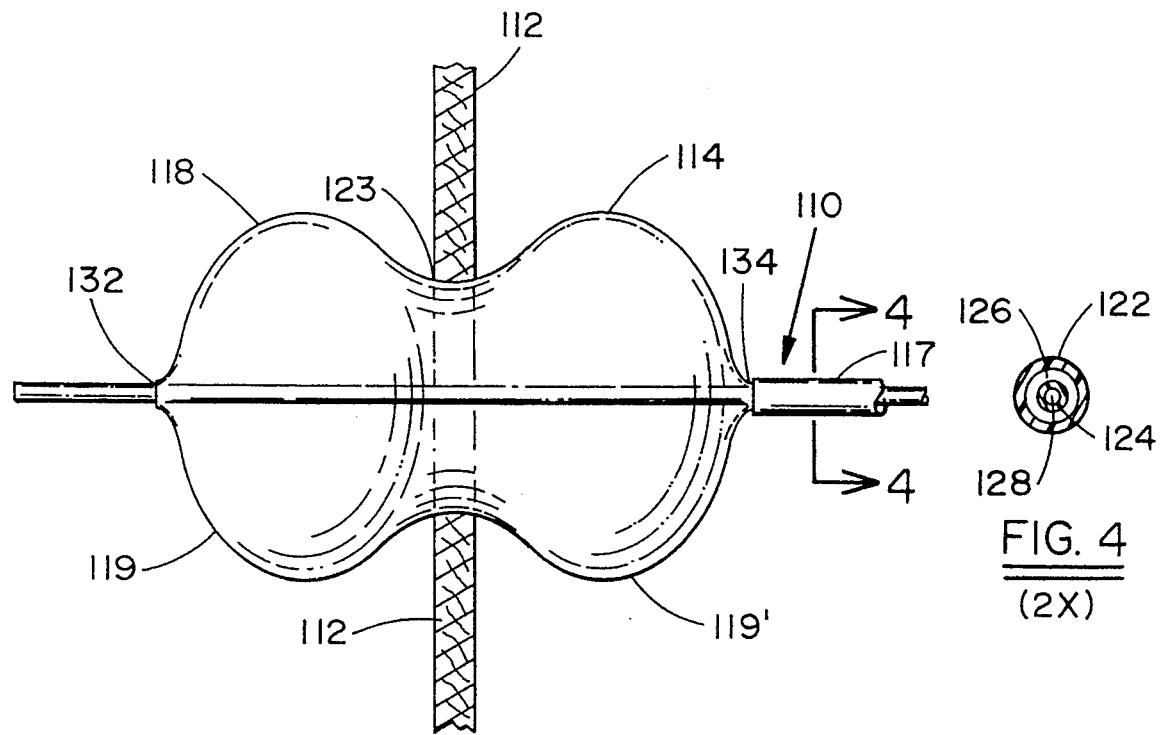
FIG. 3
FIG. 4
(2X)
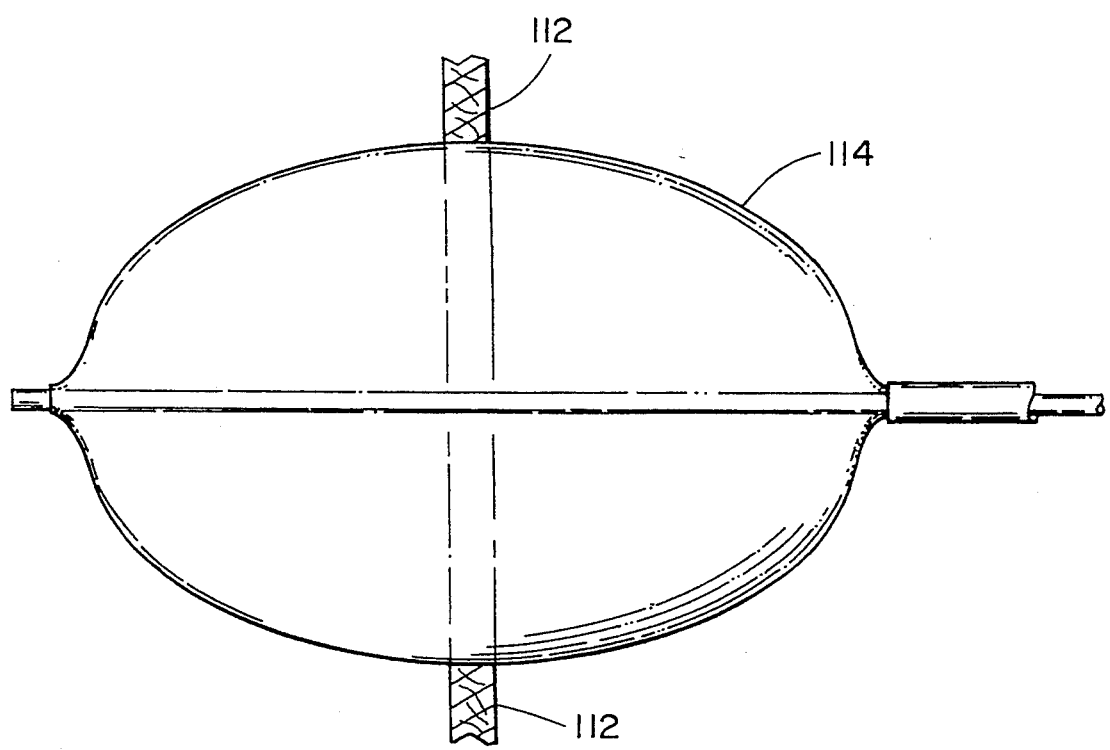
FIG. 5

5,352,199

BALLOON CATHETER

BACKGROUND OF THE INVENTION

1. Field of the Invention

This invention relates to balloon catheters for medical use. More particularly this invention relates to shape control of an inflated medical balloon catheter for specialized medical applications such as valvuloplasty and other dilating procedures.

2. Description of the Prior Art

Balloon catheters have long been used to expand hollow viscera and vascular channels. In medical applications, where an unknown, possibly variable resistance opposes the inflation of the balloon, fine control of the shape and size of the expanded balloon is desirable in order to avoid excessive deformation or the subject and more the more serious complication of rupture. In certain applications shape control is desirable to prevent axial displacement of the balloon during the dilation procedure.

This problem is addressed in Inoue, U.S. Pat. No. 4,327,736, wherein it is disclosed to apply a relatively broad rubber band about a middle portion of the tube, to restrict expansion thereof. When finally inflated, a "waist" forms in the mid portion in accordance with the differential resilience in the middle portion and the end portions of the balloon. The resultant shape is well adapted to valvuloplasty procedures, as the balloon is inhibited from slipping off the valve.

in another approach disclosed in the above noted Inoue patent the balloon is composed of two rubber layers and a cloth web or net therebetween. The relatively unyielding cloth serves to limit the size of the expanded balloon.

Both these approaches complex structural elements and are expensive and cumbersome to produce, particularly in a variety of shapes and sizes as may be medically desired.

SUMMARY OF THE INVENTION

It is therefore a primary object of the present invention to provide a balloon catheter for medical applications wherein the shape and size of the inflated balloon can be reliably controlled and to eliminate structural elements that are required in prior art devices.

It is another object of the present invention to provide a balloon catheter having a prescribed shape that can be economically manufactured.

It is yet another object of the present invention to provide an improved balloon catheter for improving the reliability of cardiac valvuloplasty procedures.

These and other objects of the present invention are attained by a balloon catheter having an axis and a lumen for transferring a fluid therethrough. The catheter includes a transaxially expandable dilation element consisting essentially of a distensible membrane attached thereto in fluid communication with a lumen for inflation, the element defining a chamber that is expanded by fluid transferred therein via the lumen. First and second regions of the chamber are defined by an imaginary plane intersecting the chamber. The distended dilation element has a prescribed shape, and when the element is inflated a pressure-volume relationship in the first region differs from the pressure-volume relationship in the second region and the inflated dilation element assumes a prescribed shape at a first inflating pressure and predictably rounds out at a second, higher inflating pressure.

According to one aspect of the invention the membrane comprises a high pressure, ultra-thin wall modified polyethylene terephthalate copolymer having thermoplastic properties and functioning as a barrier resin.

In another aspect of the invention the imaginary plane comprises two planes, and the first region comprises two noncontiguous regions that bracket the second region therebetween. A transaxial dimension of each of the noncontiguous regions increases more than a transaxial dimension of the second region when the chamber is expanded thereby forming a waist-like constriction of the inflated dilating element in the second region.

In accordance with yet another aspect of the invention, a balloon having a desired shape is fabricated from a synthetic polymer, which retains the desired shape thereafter. The balloon is formed into the desired shape by blow-molding, or otherwise, and it is attached to a catheter in fluid communication with a lumen thereof.

BRIEF DESCRIPTION OF THE DRAWING

For a better understanding of these and other objects of the present invention, reference is made to the detailed description of the invention which is to be read in conjunction with the following drawings, wherein:

FIG. 3 is a side elevation of the balloon catheter shown in FIG. 2 with the balloon inflated at a low pressure;

FIG. 4 is a sectional view taken on line 4—4 of FIG. 3; and

FIG. 5 is a side elevation of the balloon catheter shown in FIG. 2 with the balloon inflated at a higher pressure.

DESCRIPTION OF THE PREFERRED EMBODIMENT

It will be helpful in understanding the advantages of the present invention to first consider a prior art device disclosed in the above-noted Inoue patent.

Figure 1:
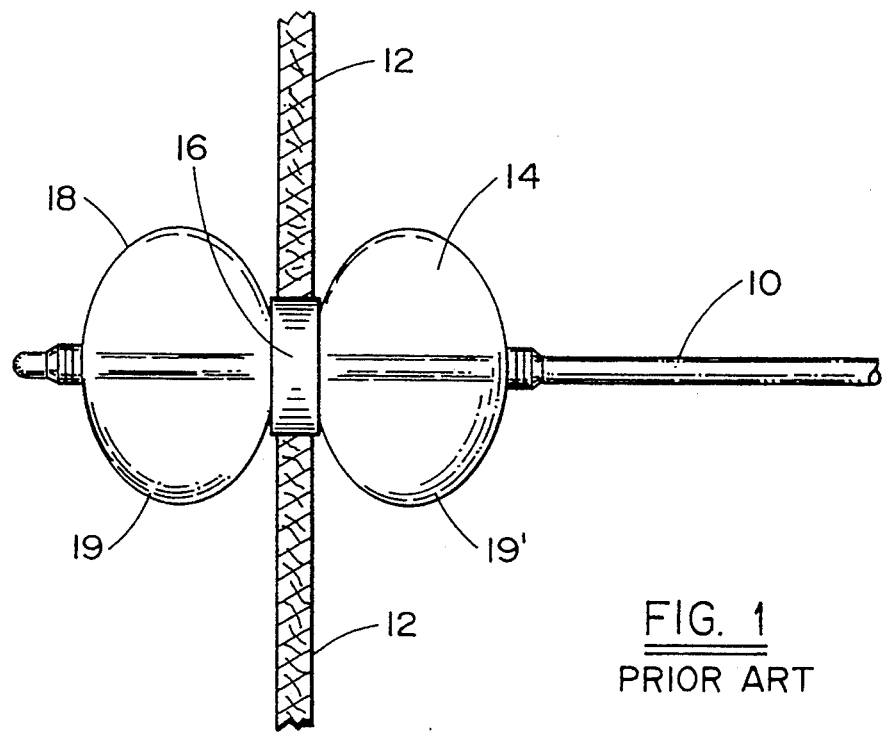
FIG. 1 is a side elevation of a balloon catheter in accordance with the prior art.

Turning to the FIG. 1 of the Drawing. 1, there is shown a balloon catheter 10 in which the balloon is positioned between two cardiac valve leaflets 12, 12. A balloon element 14 has been inflated by fluid injected through a lumen (not shown) of the catheter 10. An elastic band 16, which is stiffer than the balloon 14, is circumferentially disposed about a central portion of the balloon. The relatively strong elastic forces applied by the band 16 oppose the inflating pressure of the fluid 18 within the balloon defined by the balloon 14 to form a central constriction thereon. Continued inflation of the balloon eventually causes the transaxial dimensions of end portions 19, 19' of the balloon to exceed the diameter of the valvular orifice. Once this condition obtains, it is improbable that the balloon can be axially displaced during valvular dilatation produced by further inflation of the balloon.

The inventor has found that high pressure, ultrathin wall modified polyethylene terephthalate copolymers (PET) are particularly well suited for balloon catheters intended for medical applications, such as valvuloplasty catheters. These materials act as barrier resins. A number of such barrier resins are commercially available, and can be satisfactorily used. When a sheet of such a polymer is formed into a balloon, inflated while subjected to heat by blow-molding or the like, the balloon assumes a desired shape, which is memorized even after it cools. The copolymer has the further property that a balloon fabricated in this manner can be inflated to its memorized shape at a first pressure, and then withstand further deformation until a second pressure is reached, at which point it will predictably round out.

These properties are applied in the present invention, wherein a balloon of a desired shape is advantageously employed in specific medical applications such as valvuloplasty. Molding conditions for copolymers such as PET are known in the art, and are not the subject of the present invention. The thickness of the balloon can readily be optimized for a desired application, as the properties of the copolymer are well known.

Figure 2:
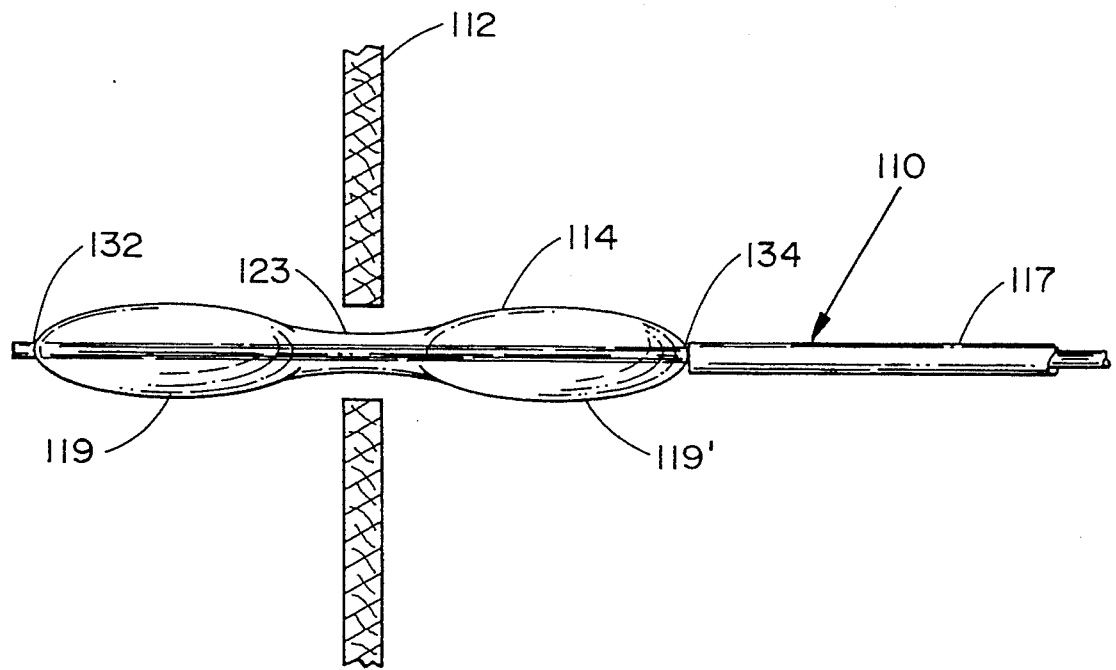
FIG. 2 is a side elevation of a balloon catheter in accordance with the invention with the balloon collapsed.

In FIGS. 2-4 there is shown a balloon catheter 110 having a proximal shaft portion 117 and a distal portion having a balloon 114 bonded thereon at proximal point 134 and distal point 132, and being generally coaxial with the catheter 110. The balloon has been fabricated as described above to have a "waist". Central portion 123 has a transaxial diameter that is less than the transaxial diameters of end portions 119, 119', as is desirable in valvuloplasty applications. Of course the balloon could be constructed in any desired shape for other medical and nonmedical dilating applications, or for the purpose of occluding a vessel or passageway having a particular configuration. The catheter 110 can be fitted with conventional radiographic markers (not shown).

Shaft portion 117 is conventional, having an outer surface 122 and an inner layer 124 which together define a central lumen 128, and a peripheral lumen 124 which communicates with the interior of balloon 114. The outer surface 122 terminates at proximal bonding point 134, while the inner layer 124 is carried through the balloon 114 and may continue beyond distal bonding point 132 to terminate at the distal end of the catheter 110. Central lumen 128 provides a passageway for a guide wire (not shown) over which the catheter is inserted. The purpose of peripheral lumen 124 is to transfer fluid therethrough under pressure for inflation and deflation of the balloon.

To use the device, the catheter 110 with the balloon 114 deflated is inserted by known techniques and positioned in a valve orifice, between valve leaflets 112, 112. A syringe or similar is attached to a conventional medical adapter (not shown) at the proximal end of the catheter, and the balloon is then inflated with a fluid 118 at a first pressure sufficient to assume its memorized shape. The expanding balloon engages the valve. As can be seen in FIG. 3, the inflated balloon retains its waist, relatively constricted central portion 123 engaging leaflets 112, 112, and thereby resisting axial displacement of the balloon 114, which could otherwise slip out of the valve orifice. Typically pressures of 40 lb/in$^2$ will distend the balloon to its memorized shape. Higher pressures are required in valvuloplasty applications, and the balloon can resist pressures of about 60 lb/in$^2$ without effacement of the central portion 123. Inflation beyond about 60 lb/in$^2$ results in effacement of the waist, the balloon assuming a generally cylindrical configuration, and thereby forcing the valve leaflets 112, 112 apart to dilate the valve, as best seen in FIG. 5.

Once dilation has been achieved, the balloon can be deflated by withdrawing its fluid contents 118 into the syringe, and the catheter may then be withdrawn. Once the balloon has been fully expanded at the higher inflation pressure, it will not return to its former waist configuration upon deflation.

Thus I provide a balloon catheter, wherein the balloon can be inflated to a desired shape and can then undergo a predictable transition to a second shape. The device lacks the encumbrances and the internal elements that are found in the prior art, and is economical to manufacture in any size as may be desired for a particular application.

While this invention has been explained with reference to the structure disclosed herein, it is not confined to the details set forth and this application is intended to cover any modifications and changes as may come within the scope of the following claims:

What is claimed is:

1. A device for cardiac valvuloplasty comprising:
   a catheter having an longitudinal axis and a lumen for transferring a fluid therethrough;
   a transaxially expandable dilation means attached to the catheter in fluid flow communication with said lumen for inflation therethrough, said dilation means consisting essentially of a distensible chamber bounded by a membrane, said chamber being inflatable at a first inflating pressure to a memorized shape comprising two end sections and a central waist therebetween that has a smaller diameter than said end sections, said waist being positionable in an orifice of a valve to be dilated, said end sections engaging upstream and downstream surfaces of the valve to restrain axial displacement of said chamber relative thereto, said waist being effaced at a second inflating pressure that is higher than said first inflating pressure to dilate the valve thereabout.

2. The device according to claim 1, wherein said membrane comprises a high pressure, ultra-thin wall modified polyethylene terephthalate copolymer.

3. The device according to claim 1, wherein said first inflating pressure is about 40 lb/in$^2$ and said second inflating pressure exceeds 60 lb/in$^2$.

4. A balloon catheter for cardiac valvuloplasty comprising:
   a distensible balloon fabricated of a heat treated synthetic polymer and being in fluid communication with a lumen of said catheter for inflation therethrough, said balloon having a memorized shape when distended at a first inflating pressure, said shape comprising two end sections and a central waist therebetween that has a smaller diameter than said end sections, said waist dimensioned to an orifice of a stenotic valve to be dilated, said end sections engaging upstream and downstream surfaces of the valve to prevent axial displacement of the balloon relative to the valve, said waist becoming rounded-out at a second inflating pressure that exceeds said first inflating pressure to dilate the valve thereabout.

5. The balloon catheter according to claim 4, wherein said first inflating pressure is about 40 lb/in$^2$ and said second inflating pressure exceeds 60 lb/in$^2$.

6. The device according to claim 1 wherein said membrane bounding said distensible chamber consists of a single layer.

* * * * *